(12) United States Patent
Schmidtke et al.

(10) Patent No.: US 9,496,467 B2
(45) Date of Patent: Nov. 15, 2016

(54) OPTOELECTRONIC COMPONENT AND METHOD FOR PRODUCING IT

(71) Applicant: OSRAM Opto Semiconductors GmbH, Regensburg (DE)

(72) Inventors: Kathy Schmidtke, Mainburg (DE); Michael Kruppa, Geisenfeld (DE); Bert Braune, Wenzenbach (DE)

(73) Assignee: OSRAM OPTO SEMICONDUCTOR GMBH, Regensburg (DE)

( * ) Notice: Subject to any disclaimer, the term of this patent is extended or adjusted under 35 U.S.C. 154(b) by 0 days.

(21) Appl. No.: 14/403,159

(22) PCT Filed: May 17, 2013

(86) PCT No.: PCT/EP2013/060293
§ 371 (c)(1),
(2) Date: Nov. 21, 2014

(87) PCT Pub. No.: WO2013/174761
PCT Pub. Date: Nov. 28, 2013

(65) Prior Publication Data
US 2015/0102374 A1    Apr. 16, 2015

(30) Foreign Application Priority Data
May 21, 2012    (DE) .......... 10 2012 104 363

(51) Int. Cl.
*H01L 33/56*    (2010.01)
*H01L 33/60*    (2010.01)
(Continued)

(52) U.S. Cl.
CPC ............ *H01L 33/56* (2013.01); *C07F 7/084* (2013.01); *C07F 7/0878* (2013.01); *C07F 7/21* (2013.01); *C08G 77/50* (2013.01); *C08L 83/14* (2013.01); *H01L 31/0203* (2013.01);
(Continued)

(58) Field of Classification Search
None
See application file for complete search history.

(56) References Cited

U.S. PATENT DOCUMENTS 3,150,601 A    9/1964    Smith et al.
3,159,602 A    12/1964    Hamilton et al.
(Continued)

FOREIGN PATENT DOCUMENTS

DE    1495919 A1    4/1969
DE    1495920 A1    6/1969
(Continued)

OTHER PUBLICATIONS

Zheng et al., "Rediscovering Silicones: Molecularly Smooth, Low Surface Energy, Unfilled, UV/Vis-Transparent, Extremely Cross-Linked, Thermally Stable, Hard, Elastic PDMS", Langmuir 2010, vol. 26, No. 24, pp. 18585-18590.

*Primary Examiner* — Calvin Choi
*Assistant Examiner* — Xiaoming Liu
(74) *Attorney, Agent, or Firm* — McDermott Will & Emery LLP

(57) ABSTRACT

An optoelectronic component is specified. According to at least one embodiment of the invention, the optoelectronic component comprises a housing (20) and a radiation-emitting or radiation-receiving semiconductor chip (10) arranged in the housing (20). Furthermore, the component comprises an optical element (50), which contains a polymer material comprising a silicone. The silicone contains at least 40% by weight of cyclic siloxanes, and at least 40% of the silicon atoms of the cyclic siloxanes are crosslinked with a further silicon atom of the silicon via alkylene and/or alkylarylene groups.

12 Claims, 5 Drawing Sheets

Figure 1:
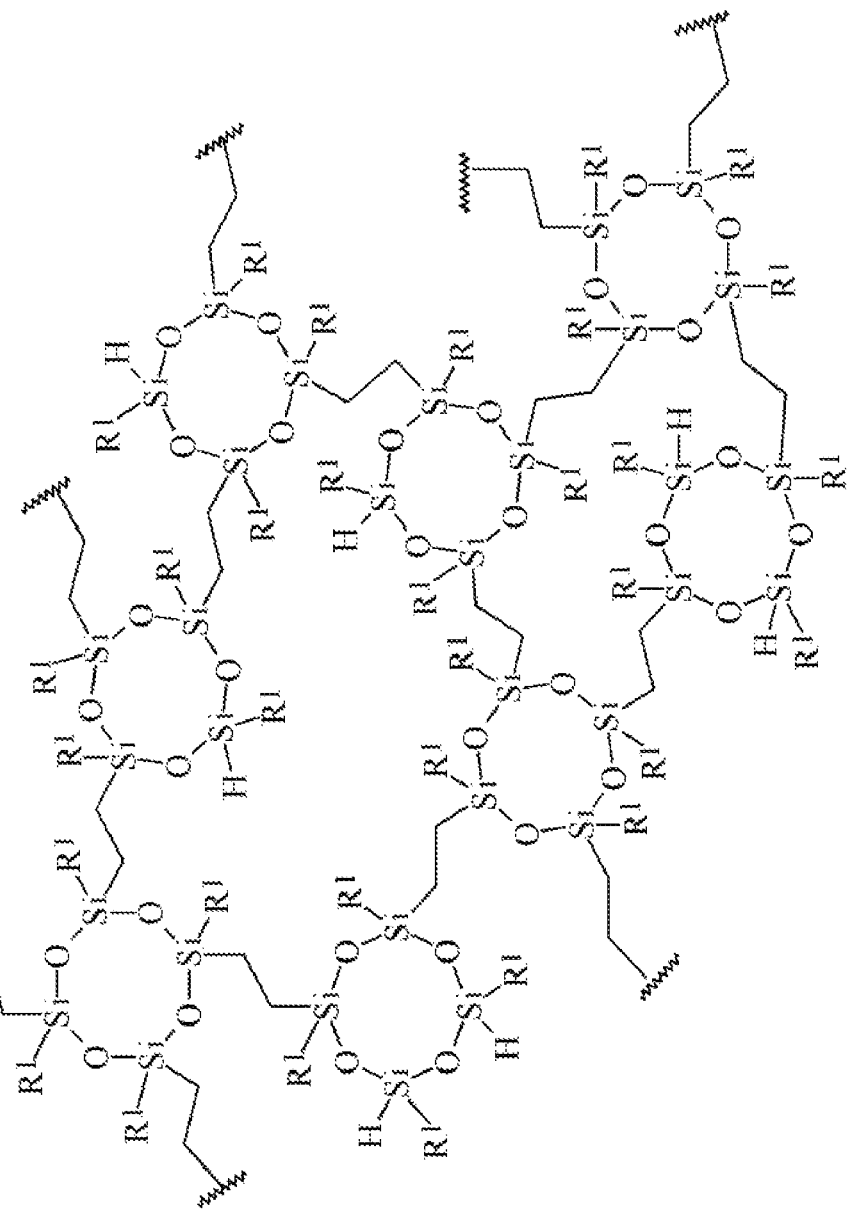

(51) Int. Cl.
  *H01L 31/0232* (2014.01)
  *C07F 7/21* (2006.01)
  *C08L 83/14* (2006.01)
  *H01L 31/0203* (2014.01)
  *C07F 7/08* (2006.01)
  *C08G 77/50* (2006.01)
  *H01L 31/18* (2006.01)
  *H01L 33/48* (2010.01)

(52) U.S. Cl.
  CPC .. *H01L 31/02322* (2013.01); *H01L 31/02327* (2013.01); *H01L 31/18* (2013.01); *H01L 33/486* (2013.01); *H01L 33/60* (2013.01); *H01L 2224/48091* (2013.01); *H01L 2224/73265* (2013.01); *H01L 2933/005* (2013.01); *H01L 2933/0033* (2013.01); *H01L 2933/0041* (2013.01); *H01L 2933/0058* (2013.01)

(56) References Cited

U.S. PATENT DOCUMENTS

| | | | |
|---|---|---|---|
| 3,197,432 A * | 7/1965 | Lamoreaux | C07F 7/0879 528/31 |
| 3,220,972 A | 11/1965 | Lamoreaux | |
| 3,377,432 A | 4/1968 | Abbott et al. | |
| 3,419,593 A | 12/1968 | Willing | |
| 3,715,334 A | 2/1973 | Karstedt | |
| 3,814,730 A | 6/1974 | Karstedt | |
| 5,334,688 A * | 8/1994 | Loo | C07F 7/20 528/15 |
| 2004/0188672 A1 | 9/2004 | Spreitzer et al. | |
| 2007/0073026 A1 | 3/2007 | Miyoshi | |
| 2009/0166665 A1* | 7/2009 | Haitko | H01L 27/14618 257/100 |
| 2010/0225010 A1 | 9/2010 | Katayama | |
| 2010/0276721 A1 | 11/2010 | Yoshitake et al. | |
| 2012/0025218 A1* | 2/2012 | Ito | H01L 33/505 257/88 |
| 2012/0056236 A1 | 3/2012 | Hamamoto et al. | |
| 2013/0075154 A1 | 3/2013 | Saito et al. | |

FOREIGN PATENT DOCUMENTS

| | | |
|---|---|---|
| EP | 0057459 A1 | 8/1982 |
| EP | 0188978 A1 | 7/1986 |
| EP | 0190530 A1 | 8/1986 |
| EP | 0905797 A2 | 3/1999 |
| EP | 1652871 A1 | 5/2006 |
| JP | 2006124710 A | 5/2006 |
| JP | 2012054383 A | 3/2012 |
| WO | 9812757 A1 | 3/1998 |
| WO | 02/13281 A1 | 2/2002 |
| WO | 2011/090361 A2 | 7/2011 |
| WO | 2011/155459 A1 | 12/2011 |

* cited by examiner

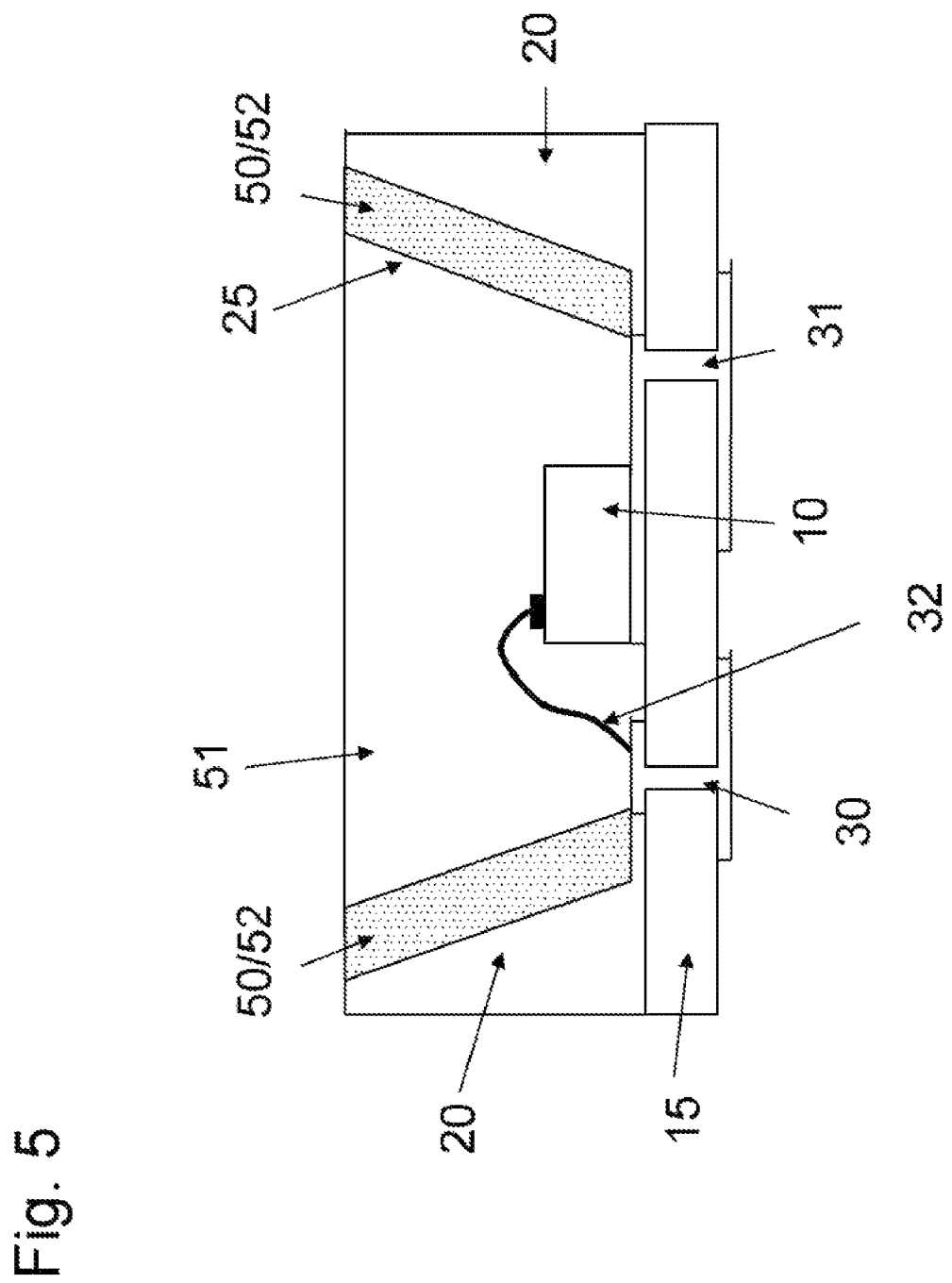

OPTOELECTRONIC COMPONENT AND METHOD FOR PRODUCING IT

The patent application relates to an optoelectronic component and to a process for producing said optoelectronic component.

In optoelectronic components, for example light-emitting diodes (LEDs), silicones are frequently used for optical elements, for example for an encapsulation. However, silicones have the disadvantage of having a tendency to yellow and crack at high temperatures, since thermal breakdown of the silicones can occur when the LED is in operation. The operating temperatures of an LED are sometimes relatively high and can occasionally exceed 120° C. In this case, stresses can build up in the optical elements made from silicones, which can lead to cracks. Yellowing and cracks can worsen the emission characteristics of an LED. Furthermore, cracks in a silicone encapsulation can allow harmful gases and moisture to penetrate and hence damage the component or lower its lifetime.

These disadvantages can occur, for example, in conventional optical elements made from poly(dimethyl-siloxane) (PDMS), which generally consists of long, substantially linear chains having few crosslinking points relative to the molecule size. In the case of conventional PDMS, thermal breakdown may, for example, follow a chain break via an intramolecular degradation mechanism, with elimination especially of trimeric siloxanes. A further disadvantage of conventional PDMS is its relatively low refractive index of about 1.41.

It is therefore desirable to develop components having silicone-containing optical elements that are less prone to thermal breakdown and, even after prolonged operation of the component, still have very good optical properties.

One problem to be solved is therefore that of specifying an optoelectronic component with a silicone-containing optical element having improved properties. A further problem is that of specifying a process for producing such an optoelectronic component.

At least one of these problems is solved by the optoelectronic component and the process for production thereof according to independent claims 1 and 13. Dependent claims specify advantageous configurations.

An optoelectronic component is specified. In at least one embodiment of the invention, the optoelectronic component comprises
- a housing;
- a radiation-emitting or radiation-receiving semiconductor chip disposed within the housing; and
- an optical element containing a polymer material comprising a silicone;

wherein the silicone contains at least 40% by weight of cyclic siloxanes and at least 40% of the silicon atoms in the cyclic siloxanes are crosslinked via alkylene and/or alkylarylene groups to a further silicon atom in the silicone.

The optoelectronic component can also be referred to hereinafter as "component" for short. "% by wt." represents percent by weight. Silicones can also be referred to as polysiloxanes. The "further silicon atom in the silicone" may be any silicon atom in a silicone. It may be part of a linear, branched or cyclic moiety of a silicone. The optical element interacts with at least some of the radiation emitted or received by the semiconductor chip.

In the "cyclic siloxanes", the cyclic structure is formed from siloxane units; cyclic structures having other bridging groups in the ring, for example an alkylene group and/or an alkylarylene group, are not cyclic siloxanes according to the application. Portions of the latter cyclic structures may, however, be formed by cyclic siloxanes in the context of the application.

According to the application, the percentage by weight of cyclic siloxane is based on the total mass of the actual silicone. Elements incorporated into the silicone, for example any fillers, are therefore not counted as part of the total mass of the silicone. The mass of the cyclic siloxanes also includes substituents which are attached only to a cyclic siloxane or merely crosslink cyclic siloxanes to one another. Substituents that a cyclic siloxane shares with another moiety other than a cyclic siloxane in the silicone, in the polymer material or in a further constituent of the component are calculated with half of their mass as part of the mass of the cyclic siloxane to which they are attached.

According to the application, the silicone in the optical element has a high proportion of cyclic siloxanes from which numerous crosslinks emanate to other silicon atoms in the silicone. The silicone therefore has a very high level of crosslinking, which is, for example, well above the level of crosslinking of conventional silicones. Because of the high level of crosslinking, the silicone has a very high thermal stability and hardness. The effect of this is that the optical element or the silicone, even after prolonged operation of the component, has only a low level of damage such as yellowing or cracking because of thermal breakdown. As a result, the lifetime of the component according to the application is increased compared to conventional components.

The cyclic siloxanes impart an astonishingly high elasticity to the silicone or to the polymer material because of their structure, and so they are not brittle and do not become porous in spite of high hardness. Advantageously, the silicone or the polymer material has an elevated thermal conductivity compared to conventional silicones because of the high level of crosslinking, since the thermal energy can better be transported or dissipated via the dense network of covalent bonds. This allows the efficiency of the component to be increased.

The type of housing is not limited according to the application, and so all types known to those skilled in the art can be used for the component. The housing of the component may comprise or be manufactured entirely from a ceramic or a heat- and radiation-resistant plastic, for example. It may additionally have a recess in which the semiconductor chip is disposed. The recess may, for example, comprise a reflector. The housing may be bonded to or comprise a carrier substrate. In addition, the component may comprise electrically conductive connections, for example leadframe, bond pad, bond wire or electrodes, in order to form contacts with the semiconductor chip.

The semiconductor chip may especially be a radiation-emitting semiconductor chip, for example an LED chip. This may be present in conjunction with a growth substrate or else take the form of a thin-film light-emitting diode chip. Examples of thin-film light-emitting diode chips are described in EP 0905797 A2 and in WO 02/13281 A1, the disclosure contents of which in this respect are hereby incorporated by reference.

The component may comprise a conversion element arranged, for example, in the form of a plaque on the semiconductor chip. The choice of converter materials for such a conversion element is not restricted according to the application; suitable converter materials are described, for example, in WO 98/12757 A1, the content of which in this respect is hereby incorporated by reference.

The component according to the application can, if it is designed to emit radiation, emit especially visible light having any color locus in the CIE diagram, especially white light. The component can therefore be used for all kinds of purposes within electronics, for example for lighting, in displays, indicators, and also in floodlights.

In a further embodiment, the polymer material is a silicone, a silicone block copolymer or a silicone-epoxide hybrid material. The statement that the polymer material comprises a silicone thus also includes aforementioned copolymers and hybrid materials. The polymer material may especially be a silicone, such that the optical element thus includes one silicone or a mixture of silicones as polymer material. It may especially contain just one highly crosslinked polysiloxane having at least 40% by weight of cyclic siloxanes. Aside from this polymer material, the optical element generally does not include any further polymer materials.

In a further embodiment, the cyclic siloxanes each independently contain three to seven silicon atoms. The cyclic siloxanes may each independently contain three to five silicon atoms, especially four silicon atoms. In this embodiment, the cyclic siloxanes thus have a moderate ring size. In addition to the significant crosslinking of the silicone, this is regarded as a further reason for the high thermal stability of the silicone. In conventional silicones that are only lightly crosslinked and contain predominantly long linear polysiloxane chains, trisiloxanes can be eliminated via an intramolecular mechanism. This breakdown mechanism, which is known per se, can occur only to an extremely limited degree, if at all, in the cyclic siloxanes, and so a chain break in the silicone causes only minor thermal breakdown, if any. Thus, a significant overall improvement in thermal stability of the silicone is obtained compared to lightly crosslinked, substantially linear polysiloxanes.

In a further embodiment, at least 50% of the silicon atoms in the cyclic siloxanes are crosslinked via alkylene and/or alkylarylene groups to a further silicon atom in the silicone. Such crosslinking may be present in at least 55%, especially at least 60%, of the silicon atoms in the cyclic siloxanes. It follows from this that at least every second silicon atom in the cyclic siloxanes constitutes a crosslinking site in the silicone, which leads to an extremely highly crosslinked silicone.

In a further embodiment, the silicone contains at least 75% by weight of cyclic siloxanes. The silicone may also consist to an extent of at least 90% by weight or even entirely of cyclic siloxanes. It is optionally possible to add small amounts of substantially linear polysiloxanes with low branching to the silicone, for example for dilution. In this embodiment, the polymer material generally corresponds to the silicone.

A silicone in this embodiment is notable for a very high thermal stability and hardness, and for a high elasticity, which brings the above-described advantages. The hardness can be determined by means of nanoindentation to be about 0.34 GPa. A measure reported for the elasticity is the modulus of elasticity, which can be determined for this embodiment by means of a tensile test to be about 1.3 GPa to 1.7 GPa. The high thermal stability is also manifested by the fact that only a very small loss of mass occurs in the course of prolonged heating to high temperatures. For example, the weight loss at 300° C. is less than 1% when heating from room temperature at 10 K/min (TGA measurement). Nanoindentation, tensile testing and TGA measurement are methods known to those skilled in the art for determining properties of polymer materials.

In addition, such a silicone has a low surface energy and low tack. It is therefore not very sensitive to dust and is therefore suitable for forming an outer surface of the component. Advantageously, in the production of the component, it is possible to dispense with additional vitrification of the surface by means of plasma, as necessary in the case of conventional silicones, and to omit the corresponding operation.

In a further embodiment, the cyclic siloxanes are represented by a structure of the formula I

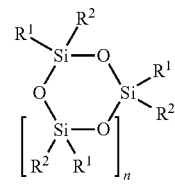

where
n is selected from 1, 2, 3, 4 and 5,
$R^1$ is in each case independently selected from a group comprising alkyl, cycloalkyl and aryl,
$R^2$ is in each case independently selected from a group comprising alkylene and/or alkylarylene group, hydrogen atom, a substituent of the formula

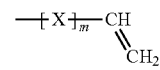

with m=0 or 1 and X=$C_1$-$C_4$-alkylene or phenylene, and an attached heteroatom, and
where at least 40% of the $R^2$ substituents correspond to the alkylene and/or alkylarylene group, through which the $R^2$-substituted silicon atom in the cyclic siloxane of the formula I is crosslinked to a further silicon atom in the silicone, and the alkylene and/or alkylarylene group in each case independently has a structure of the following formula

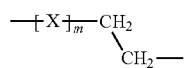

with m=0 or 1 and X=$C_1$-$C_4$-alkylene or phenylene.

It is also possible for at least 50%, especially 55%, of the $R^2$ substituents to correspond to one of the above-described alkylene and/or alkylarylene groups. It is occasionally even possible for at least 60% of the $R^2$ substituents to correspond to such an alkylene and/or alkylarylene group.

The $R^2$ substituents that do not correspond to an alkylene and/or alkylarylene group, through which the $R^2$-substituted silicon atom in the cyclic siloxane of the formula I is crosslinked to a further silicon atom in the silicone, may correspond to uncrosslinked functional groups from which the alkylene and/or alkylarylene groups are formed during curing. If $R^2$ is none of the above-described alkylene and/or alkylarylene groups, $R^2$ may generally, for example to an extent of at least 90%, be a hydrogen atom. An attached heteroatom may already be present prior to curing or, for example, may also be introduced by subsequent hydrolysis of an Si—H bond, and so the heteroatom is especially an oxygen atom. There may also be a further bond via a heteroatom to a further silicon atom in the silicone. In principle, the heteroatom may also bear further substituents, for example a hydrogen atom.

The expression "$C_1$-$C_4$-alkylene" represents an alkylene group which may contain 1, 2, 3 or 4 carbon atoms (C atoms), i.e. methylene, ethylene, propylene or butylene. This notation is known per se to those skilled in the art and is also used analogously for other substituents. In the formula specified for the alkylene and/or alkylarylene group, the unlabeled bonds correspond to the binding sites of this group to silicon atoms, and the orientation may be as desired. It is especially possible that m=0, so that the bridge is via an ethylene group. On the other hand, the mechanical properties of the silicone and/or refractive index thereof can be modified via the X group with m=1.

In addition, in formula I, n may in each case independently be 1, 2 or 3, especially 2. These siloxanes are generally more thermally stable than the larger cyclic siloxanes.

In a further development of this embodiment, the optical element is obtainable by curing a composition comprising a first cyclic siloxane represented by the formula II and a second cyclic siloxane represented by the formula III

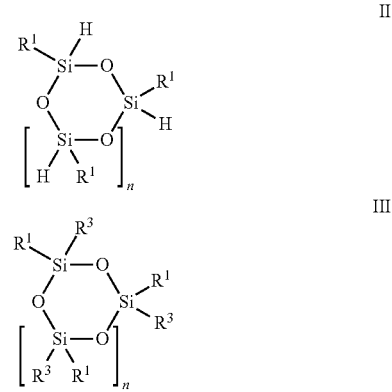

where, in formula II or in formula III,
n is in each case independently selected from 1, 2, 3, 4 and 5,
$R^1$ is in each case independently selected from a group comprising alkyl, cycloalkyl and aryl, and
$R^3$ is in each case independently a substituent which is represented by the following formula

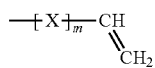

with m=0 or 1 and X=$C_1$-$C_4$-alkylene or phenylene.

In formula II or in formula III, in each case independently, n=1, 2 or 3, especially n=2. It is especially possible, as described above, that m=0. Advantageously, in the first or second cyclic siloxane, every silicon atom bears a group suitable for crosslinking, and so these cyclic siloxanes are ideally suited to silicones having a high level of crosslinking. The first cyclic siloxane can be used in a ratio relative to the second cyclic siloxane of ≥1, such that generally hydrogen atoms and very much less commonly $R^3$ substituents may be present in the cyclic siloxanes of the formula I as nonbridging $R^2$ substituents.

The composition may additionally comprise a catalyst, for example a platinum catalyst. In the course of curing, the first cyclic siloxane (see formula II) crosslinks with the second cyclic siloxane (see formula III), which can be effected, for example, via a hydrosilylation. A suitable catalyst is, for example, the Karstedt catalyst. The reaction of an Si—H bond with an $R^3$ substituent can form an $R^2$ substituent corresponding to an alkylene and/or alkylarylene group, such that the crosslinking forms cyclic siloxanes represented by formula I from the first and second cyclic siloxanes. Traces of the catalyst can—possibly even in the finished component—be detected in the silicone in the optical element.

The level of crosslinking in the silicone, the proportion of cyclic siloxanes in the silicone and the substituents in the cyclic siloxanes can be determined and detected by NMR spectroscopy. This can be accomplished, for example, by means of solid-state NMR, especially selected from a group comprising $^1$H, $^{13}$C and $^{29}$Si NMR. Detection is also possible in principle in a finished component, for example on sections through the optical element.

In a further embodiment, $R^1$ is in each case independently selected from a group comprising $C_1$-$C_4$-alkyl, $C_5$-$C_6$-cycloalkyl and phenyl. In this case, $R^1$ may especially be selected from a group comprising methyl, cyclohexyl and phenyl. $R^1$ may especially be methyl, and so a highly crosslinked poly(dimethylsiloxane) is effectively obtained as the silicone. Compared to conventional PDMS having low branching, this especially features elevated thermal stability. With $R^1$=methyl, an inexpensive silicone which is easy to process is especially obtained. Similarly to conventional PDMS, such a silicone has a comparatively low refractive index of about 1.42.

An advantageous example of such a silicone can be formed by curing a composition containing first cyclic siloxanes of the formula II and second cyclic siloxanes of the formula III, especially in a ratio of 1.8:1 to 2.2:1, for example 2:1, where in formula II and in formula III n=0, m=0 and $R^1$=methyl. In that case, the silicone includes cyclic siloxanes of the formula I with n=0, m=0 and $R^1$=methyl. The polymer material in this case may especially be the silicone itself, which may consist to an extent of at least 90% by weight or entirely of the cyclic siloxanes of the formula I. In this example, a highly crosslinked poly(dimethylsiloxane) is obtained as polymer material. The silicone according to this example has a modulus of elasticity of about 1.3 GPa to 1.7 GPa (tensile test). The hardness is about 0.34 GPa (nanoindentation).

The refractive index of the silicone can be adjusted via the substituents on the silicon atoms. Polysiloxanes having numerous methyl groups have a low refractive index. With higher alkyl groups or cycloalkyl groups and aromatic substituents, the refractive index of a silicone can be increased. It is therefore possible, for example, to control the refractive index of the silicone with a combination of methyl groups and cyclohexyl groups or phenyl groups, which can be accomplished via the ratio of these substituents. The refractive index can be matched, for example, to any filler, in order to optimize the light emission or to increase the transparency of an optical element.

In an alternative embodiment, $R^1$ is independently selected from a group comprising $C_2$-$C_4$-alkyl, $C_5$-$C_6$-cycloalkyl and phenyl. $R^1$ may be selected independently from a group comprising cyclopentyl, cyclohexyl and phenyl. $R^1$ may especially be cyclohexyl and/or phenyl. In this embodiment, the cyclic siloxane does not contain any methyl groups, but only higher (cyclo)alkyl groups or phenyl groups. The silicone in this embodiment generally has a higher refractive index than is the case for silicones containing methyl groups. The higher refractive index of the silicone can, for example, improve the emission of light from the component.

In general, polysiloxanes having higher alkyl groups, cycloalkyl groups or phenyl groups as substituents have lower thermal stability than methyl-substituted silicones. This negative property can at least substantially be compensated for in a component according to the application because of the high level of crosslinking of the silicone. The component according to the application may therefore comprise an optical element containing or consisting entirely of a highly refractive and nevertheless thermally stable silicone.

In a further embodiment, at least 40% of the $R^1$ substituents are each independently selected from a group comprising $C_5$-$C_6$-cycloalkyl and phenyl. It is possible for at least 60%, especially at least 80%, of the $R^1$ substituents to be selected from this group. It is also possible for all the $R^1$ substituents to be selected from this group. A silicone in this embodiment especially has a higher refractive index than a methyl-substituted silicone.

In a further embodiment, the silicone therefore has a refractive index n greater than or equal to 1.44. The refractive index n of the silicone may be greater than or equal to 1.46, especially greater than or equal to 1.48. If the silicone has a high proportion of phenyl groups, the refractive index n may even be greater than or equal to 1.50. Compared to conventional PDMS, which has a refractive index of n=1.41, it is possible to obtain much better emission of light with this silicone. In addition, the refractive index can be matched to any filler. $SiO_2$ particles, for example, have a refractive index n of about 1.46.

All figures for refractive indices, in accordance with the application, are based on a wavelength of 632 nm and a temperature of 25° C. (room temperature). The refractive index can be abbreviated to "n"; it is determined with a refractometer.

In a further embodiment, the optical element is transparent to the radiation used in the component. The optical element may thus be transparent or at least translucent to the radiation used, which is understood to mean a relative transmission of at least 50%, especially at least 80%. Such an optical element is especially disposed in a beam path of the component.

"Beam path of the component" is understood to mean possible paths through which radiation can pass or be emitted by the semiconductor chip from the component. According to the application, the terms "beam path" and "beam path of the component" are used synonymously.

In a further embodiment, the optical element is an encapsulation that encases the semiconductor chip. The semiconductor chip may also be directly encased by the encapsulation or the optical element. Because of the improved mechanical properties of the silicone, which is very thermally stable, hard and elastic and has improved thermal conductivity, it has very good suitability for encapsulation of semiconductor chips, even if they generate very high temperatures in operation, for example greater than 120° C. In a component according to this embodiment, the semiconductor chip is generally disposed in the recess of a housing, and the encapsulation is transparent to the radiation emitted. The recess may then, for example, be sealed with the optical element as an encapsulation and can protect the semiconductor chip from harmful environmental influences.

In a further embodiment, the optical element comprises a lens. The optical element in this case may be a separately produced lens which is disposed subsequently on the component. For this purpose, for example, an adhesive may be used. Such a lens can, for example, be cast and cured in a mold (called molding). However, the optical element may also, as described above, be an encapsulation which encases the semiconductor chip and is partly shaped to form the lens.

In a further embodiment, the optical element comprises an inorganic filler which has been embedded in the polymer material and is selected from a group comprising thermally conductive particles, a diffuser, a converter material and a combination thereof. It may especially comprise a converter material. The inorganic filler may account for 10% to 80% by weight, especially 20% to 60% by weight, of the optical element. The inorganic filler may be present in particles which comprise or consist of the inorganic filler. The optical element, apart from a few further additives, may consist for the most part (greater than 95% by weight) of the polymer material and the inorganic filler.

Thermally conductive particles may, for example, be selected from a group comprising $SiO_2$ particles, for example cristobalite, aluminum oxide ($Al_2O_3$), aluminum nitride (AlN), zirconium oxide ($ZrO_2$) and combinations thereof. It is especially possible to use $SiO_2$ particles, for example in the form of spherical $SiO_2$ particles. The thermally conductive particles have a higher thermal conductivity than a silicone and can thus further increase the thermal conductivity of the optical element. The refractive index of the silicone or of the polymer material can, for example, be matched to $SiO_2$ particles, such that, for example, barely any scatter, if any at all, occurs during operation at these particles. However, it is also possible to deliberately establish a difference in the refractive indices, in order to achieve a well-defined scatter or appealing emission characteristics.

With a diffuser in the optical element, it is possible to improve the emission of light. The diffusers may, for example, be selected from a group comprising $TiO_2$, $ZrO_2$, $Al_2O_3$ and combinations thereof. One example of such a combination is an $Al_2O_3$-coated $TiO_2$ particle, such that $TiO_2$-catalyzed breakdown reactions are suppressed.

The choice of converter materials is not restricted in accordance with the application, and so all converter materials suitable for volume conversion may be used in this embodiment. Examples of such converter materials are described in WO 98/12757 A1, the content of which in this respect is hereby incorporated by reference. The converter material may be present as a constituent of particles, for example together with binders. The particles may also consist of the converter material.

The heat generated by conversion can be dissipated efficiently because of the improved thermal conductivity of the silicone or of the polymer material, which is attributable to the high level of crosslinking in the silicone. This results in a stable color locus for the light emitted by the component. The thermal conductivity can optionally be increased further, as described above, by means of thermally conductive particles.

As an alternative to an optical element disposed in the beam path which is transparent to the radiation used, the component according to the application, in a further embodiment, may include an optical element that takes the form of a reflector and contains a reflective filler. For example, the optional element may contain 10% to 80% by weight, especially 20% to 60% by weight, of reflective filler. Reflective fillers used may, for example, be $TiO_2$, $ZrO_2$, $Al_2O_3$ and combinations thereof.

In a development of this embodiment, the housing has a recess in which the semiconductor chip is disposed, in which case the optical element lines at least part of the recess or forms at least part of the housing in the region of the recess. In principle, it is also possible for the entire housing to contain the polymer material and to comprise reflective fillers at least in the region of the recess, such that a reflector is again obtained as the optical element. The recess can be sealed with an encapsulation which may, for example, be a conventional encapsulation or else a further optical element according to at least one embodiment of the application.

As a further aspect of the application, a process for producing an optoelectronic component having an optical element is provided. In at least one embodiment, the process comprises the steps of:

A) providing a housing;

B) disposing a radiation-emitting or radiation-detecting semiconductor chip within the housing;

C) producing an optical element containing a polymer material comprising a silicone;

wherein the silicone contains at least 40% by weight of cyclic siloxanes and at least 40% of the silicon atoms in the cyclic siloxanes are crosslinked via alkylene and/or alkylarylene groups to a further silicon atom in the silicone.

The process for producing the component is also referred to as "process" for short. By means of the process, it is possible to produce a component according to at least one embodiment of the application. The embodiments of the component described herein and the properties thereof therefore also apply in an equivalent manner to the embodiments of the process according to the application and vice versa.

The sequence of process steps A), B) and C) is guided by the embodiment of the component which is to be produced. For a component having an optical element in the beam path, the sequence of A), B) and C) specified here can be used. If necessary, in an embodiment having an optical element in the form of a reflector, the sequence of steps B) and C) can also be altered. The optical element is especially produced such the occurs in interaction with the radiation emitted or received by the semiconductor chip. If it can be produced separately, for example in the case of a positionable lens, step C) also includes an arrangement of the optical element in the component such that such an interaction is possible.

In a further embodiment of the process, the optical element is produced in step C) by curing a composition comprising a first cyclic siloxane represented by the formula II and a second cyclic siloxane represented by the formula III

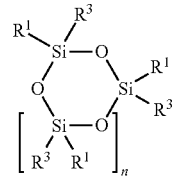

II

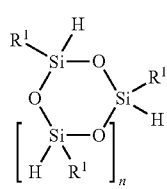

III where, in formula II or in formula III, n is in each case independently selected from 1, 2, 3, 4 and 5, and $R^1$ is in each case independently selected from a group comprising alkyl, cycloalkyl and aryl, and $R^3$ is in each case independently a substituent which is represented by the following formula

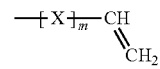

with m=0 or 1 and X=$C_1$-$C_4$-alkylene or phenylene.

In the course of curing of the composition, cyclic siloxanes represented by the formula I may be formed. It is possible for the above-described modifications and developments of the cyclic siloxanes of the formulae I, II and III to be used or formed correspondingly.

The crosslinking of the first cyclic siloxane with the second cyclic siloxane can be effected via a hydrosilylation. For this purpose, the composition may contain a catalyst, for example a platinum catalyst. For example, the composition may contain 1 to 100 ppm of a platinum catalyst. Platinum catalysts used may be $H_2PtCl_6$, complexes of platinum with vinyl-containing organosiloxanes, for example the Karstedt catalyst, and complexes of platinum with other organic ligands. Platinum complexes with vinyl-containing organosiloxanes are described in U.S. Pat. No. 3,419,593, U.S. Pat. No. 3,715,334, U.S. Pat. No. 3,377,432 and U.S. Pat. No. 3,814,730, the disclosure contents of which in this respect are hereby incorporated by reference. Platinum complexes with other organic ligands are described in U.S. Pat. No. 3,150,601, U.S. Pat. No. 3,159,602, U.S. Pat. No. 3,220,972, EP 0 057 459, EP 0 188 978 and EP 0 190 530, the disclosure contents of which in this respect are hereby incorporated by reference.

In a further embodiment, the ratio of first cyclic siloxane to second cyclic siloxane in the composition is in the range from 1:1 to 4:1, especially from 1.2:1 to 3:1. The ratio may be 1.3:1 to 2.5:1, especially 1.8:1 to 2.2:1, for example 2:1. Thus, in particular, more first cyclic siloxanes than second cyclic siloxanes are used in the composition. In the course of curing of the composition, the vinyl groups in the $R^3$ substituents are therefore substantially or fully depleted and form bridging groups, alkylene and/or alkylarylene groups. "Substantially" means at least 90%, especially at least 98%. This is advantageous, since remaining vinyl groups can enter into disruptive reactions or decompositions in the optical element. However, unreacted hydrogen atoms may still remain in the silicone as $R^2$ substituents in the cyclic siloxanes of the formula I, which is attributable to the above-described conditions. In contrast to vinyl groups, however, Si—H bonds are (substantially) harmless to the lifetime and quality of the optical element.

In a further embodiment, the composition contains at least one further crosslinkable polymer component. Such a crosslinkable polymer component may be a polysiloxane which is used, for example, for dilution. In addition, when the polymer material is, for example, a silicone-epoxide hybrid material or a silicone block copolymer, this may also be a non-silicone crosslinkable polymer component. For this purpose, it is optionally possible to use conventional materials known to those skilled in the art. However, the polymer material may preferably be a silicone, and so it is possible to substantially or entirely dispense with other crosslinkable polymer materials in the composition.

In a further embodiment, the composition comprises at least one of the group comprising adhesion promoter, catalyst inhibitor, yellowing stabilizer and thixotropic agent. For these additives, it is possible to use conventional compounds already known to those skilled in the art that are generally used for production of silicones or silicone-containing polymer materials.

Examples of inhibitors are polyorganosiloxanes, especially cyclic siloxanes in which at least one alkyl group has been replaced by an alkenyl group, for example trimethylvinyltetrasiloxane, pyridine, phosphines, organic phosphites, unsaturated amides, alkyl-containing maleates, acetylene alcohols and combinations thereof. Examples of acetylene alcohols are 1-ethynyl-1-cyclohexanol, 3-methyl-1-dodecyn-3-ol, 3,7,11-trimethyl-1-dodecyn-3-ol, 1,1-diphenyl-2-propyn-1-ol, 3,6-diethyl-1-nonyn-3-ol and 3-methyl-1-pentadecyn-3-ol, and 1-ethynyl-1-cyclohexanol in particular is used.

Examples of adhesion promoters are alkoxy-containing organosilanes, for example vinyltrimethoxysilane, (3-methacryloyloxypropyl)trimethoxysilane, (3-glycidoxy-propyl)trimethoxysilane and combinations thereof.

In a further embodiment, curing in step C) is effected by heating to more than 140° C. for at least one hour. It is possible to cure by heating to more than 150° C. for at least 3 hours, especially at least 5 hours. In this case, it is possible to observe at least three different, generally rising temperature levels. This serves for production of a very substantially stress-free and blister-free optical element.

The invention is illustrated in detail hereinafter with reference to the drawings, especially using working examples. In these, elements that are identical or equivalent or have the same effect are given the same reference symbols. The figures and the size ratios of the elements shown in the figures with respect to one another should not be regarded as being to scale. Instead, individual elements may be shown in oversized form for better clarity and/or for better comprehensibility and/or in simplified form.

Figure 2:
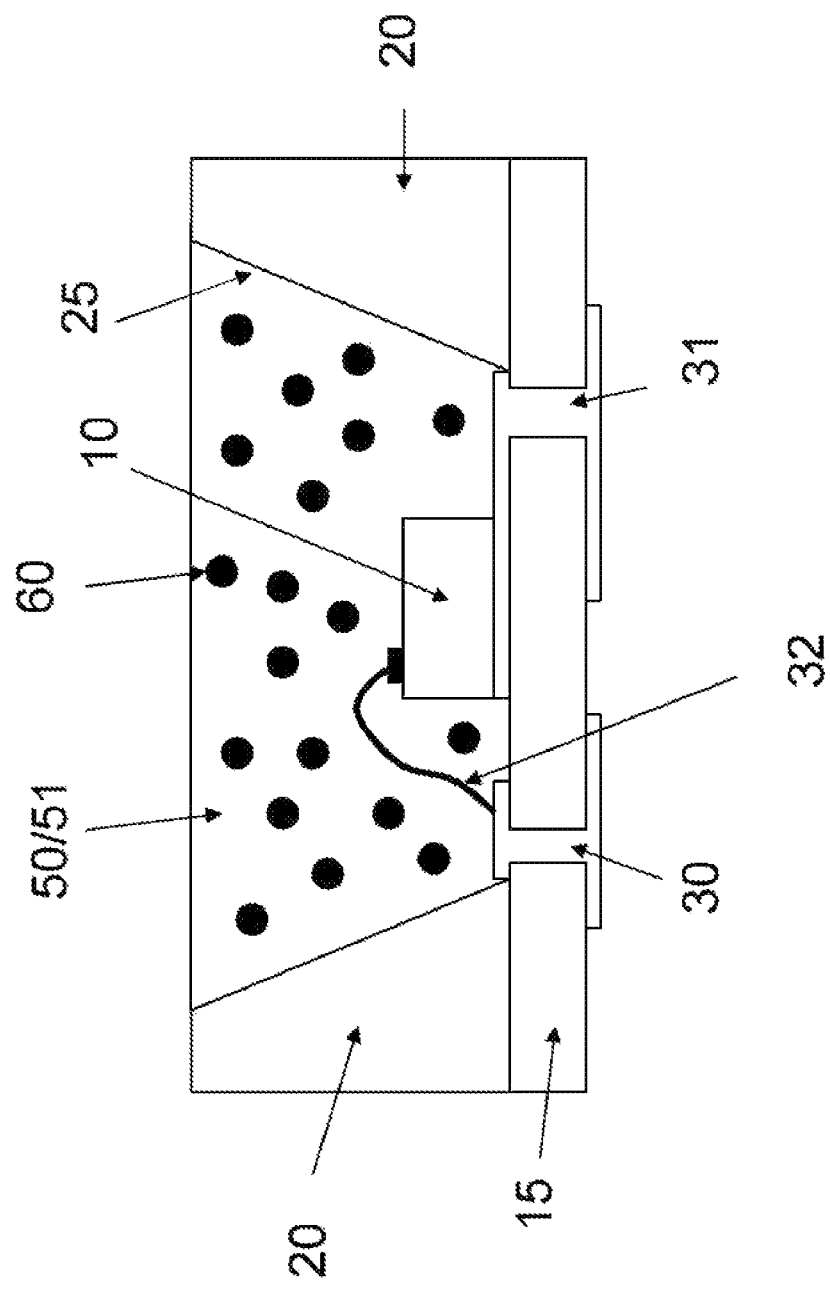
Figure 3:
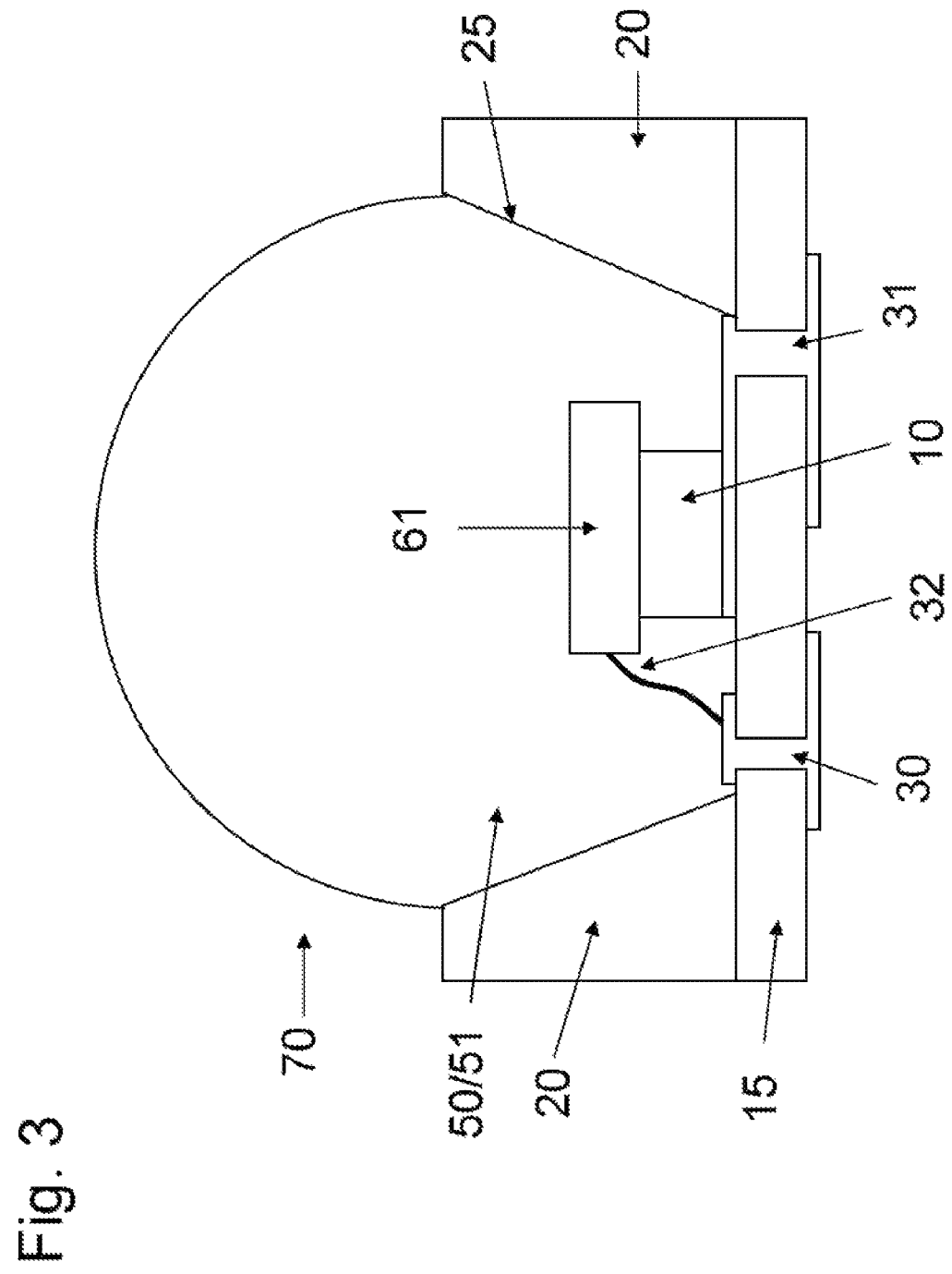
Figure 4:
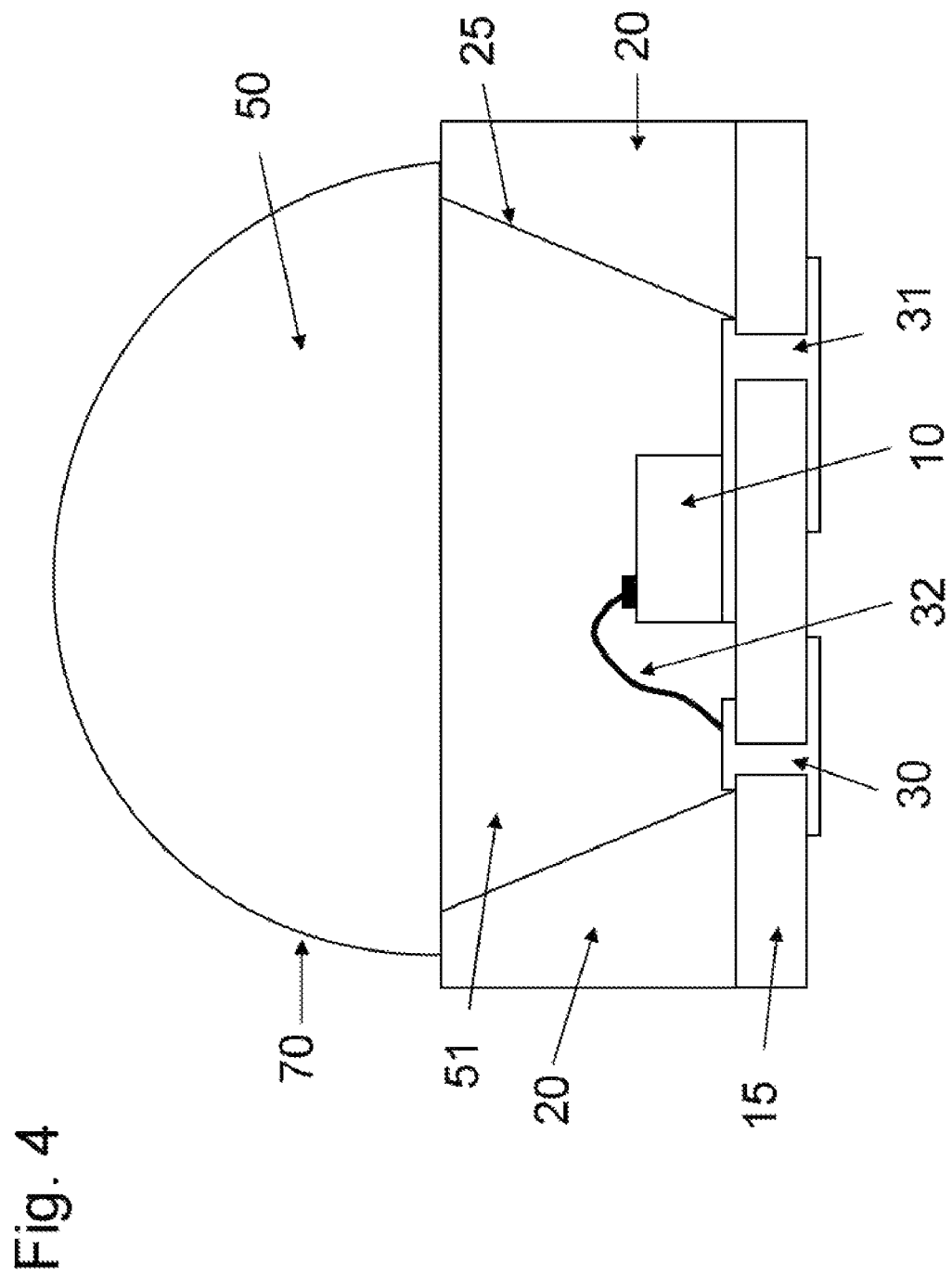

The figures show:

FIG. 1 a detail from a silicone in an optical element,

FIG. 2 a schematic cross section through a component with an optical element for volume conversion, FIG. 3 a schematic cross section through a component with an encapsulation shaped to a lens as the optical element, FIG. 4 a schematic cross section through a component in which a separately formed lens has been positioned as an optical element, FIG. 5 a schematic cross section through a component with an optical element in the form of a reflector.

FIG. 1 shows a detail from a silicone as may occur in an optical element of the component in one embodiment of the application. The crosslinked cyclic siloxanes shown correspond to siloxanes of the formula I, where n=2 and m=0 throughout in this example. The bridging alkylene and/or alkylarylene groups ($R^2$ in formula I) are therefore ethylene bridges, which are shown in reduced form in FIG. 1 for the sake of clarity.

Such a silicone is obtainable, for example, by platinum-catalyzed hydrosilylation reaction of a first cyclic siloxane of the formula II with n=2 and a second cyclic siloxane of the formula III with n=2 and m=0 by curing a corresponding composition. The ratio of first cyclic siloxane to second cyclic siloxane may be in the range from 1:1 to 4:1, especially from 1.2:1 to 3:1, preferably from 1.3:1 to 2.5:1, and may, for example, be 2:1. If the first cyclic siloxane is used in excess, the silicone has barely any vinyl groups any longer, if any at all. In that case, however, Si—H bonds are generally still present, corresponding to one $R^2$=hydrogen atom in formula I. In contrast to vinyl groups and olefins, Si—H bonds are generally unproblematic with regard to thermal decompositions.

The silicone shown in FIG. 1 is rich in cyclic siloxanes; it may contain, for example, at least 40% by weight, especially at least 75% by weight or even at least 90% by weight of cyclic siloxanes, or even consist entirely thereof. In addition, the silicone has a high level of crosslinking, since at least 40%, especially at least 50% or even at least 60% of the silicon atoms in the cyclic siloxanes are crosslinked with a further silicon atom via an ethylene group. In general, the further silicon atom in this example is likewise part of a cyclic siloxane.

The refractive index of the silicone is guided especially by the $R^1$ substituents. $R^1$ is selected from alkyl, cycloalkyl and aryl and may especially be $C_1$-$C_4$-alkyl, $C_5$-$C_6$-cycloalkyl or phenyl. A highly refractive silicone can be obtained when at least 40% of the $R^1$ substituents are selected from $C_5$-$C_6$-cycloalkyl and phenyl.

A further advantageous example of a silicone from FIG. 1 can be formed by curing a composition containing first cyclic siloxanes of the formula II and second cyclic siloxanes of the formula III, especially in a ratio of 1.8:1 to 2.2:1, for example 2:1, where n=0, m=0 and $R^1$=methyl in formula II and in formula III. In that case, the silicone according to FIG. 1 has $R^1$=methyl throughout, which corresponds to crosslinked cyclic siloxanes of the formula I with n=0, m=0 and $R^1$=methyl. The polymer material in this case may especially be the silicone itself, which may consist to an extent of at least 90% by weight or entirely of the cyclic siloxanes of the formula I. In this example, a highly crosslinked poly(dimethyl-siloxane) is obtained as polymer material. In this example, more than 60%, especially more than 65%, of the silicon atoms in the cyclic siloxanes may be crosslinked to a further silicon atom via an ethylene bridge. The silicone may have a modulus of elasticity of 1.3 GPa to 1.7 GPa (tensile test). The hardness may be about 0.34 GPa (nanoindentation).

FIG. 2 shows a component according to one embodiment of the application, using the example of an LED. The component here comprises a housing 20 in conjunction with a carrier substrate 15. The housing 20 may comprise a ceramic or a heat- and radiation-resistant plastic. In a recess 25 in the housing 20 is disposed a semiconductor chip 10 which emits radiation when the component is in operation. The side walls of the recess 25 are tapered here and may include a reflective material. The semiconductor chip 10 can be supplied with power via electrically conductive contacts 30, 31 and a bonding wire 32.

The component has an optical element 50 made from a polymer material which fills the recess 25 of the housing 20 and encases the semiconductor chip 10 here as encapsulation 51. The optical element 50 is transparent here to the radiation emitted by the semiconductor chip 10 and can be shaped as a lens (not shown). In the example according to FIG. 2, particles 60 comprising one or more converter materials are present in homogeneous distribution as inorganic filler in the polymer material (called volume conversion). Alternatively or additionally, the component may include a conversion element which may be disposed, for example, in the form of a plaque on the semiconductor chip 10 (not shown). In addition, further inorganic fillers such as diffusers or thermally conductive particles, for example $SiO_2$ particles, may be distributed within the polymer material of the optical element 50. The inorganic fillers can make up 10% to 80% by weight of the optical element 50. The component may emit visible light with any color impression, especially white light.

The polymer material comprises a silicone and may especially consist of silicone. The silicone may correspond to a silicone according to FIG. 1. It comprises at least 40% by weight of cyclic siloxanes. In addition, the silicone is highly crosslinked, since at least 40% of the silicon atoms in the cyclic siloxanes are crosslinked via alkylene and/or alkylarylene groups to a further silicon atom in the silicone. Because of the high level of crosslinking, the silicone is stable to thermal decomposition, is hard, has elevated thermal conductivity and is advantageously also elastic.

The optical element 50 is barely impaired, if at all, by the heat evolved by the semiconductor chip 10 and by the converter material, and therefore has no tendency to yellow or crack. The component is therefore well-protected from harmful environmental influences and has a long lifetime. As required, via the choice of substituents in the silicone, especially of the cyclic siloxanes, the refractive index of the silicone or of the optical element 50 can be adjusted. With highly refractive silicones having, for example, a refractive index of at least 1.44, it is possible to improve the emission of light compared to conventional PDMS.

FIG. 3 shows a component in a further embodiment in cross section. It corresponds substantially to the component from FIG. 2. Rather than particles 60 comprising converter materials, a conversion element 61 is disposed here on the semiconductor chip 10. The optical element 50 is formed here as a lens 70 which can overlap the housing 20.

FIG. 4 shows a component according to a further embodiment of the application in cross section. It comprises, as optical element 50, a lens 70 disposed on the component, for example by means of an adhesive. The optical element 50 comprises a silicone according to at least one embodiment of the application. Such a lens 70 can be cast and cured separately, for example in a mold. The semiconductor chip 10 in this example has been encased with an encapsulation 51 which fills the recess 25. The encapsulation 51 may likewise be an optical element according to one embodiment application or consist of conventional materials. The component may comprise converter materials, for example in the form of particles or of a plaque (not shown here).

FIG. 5 shows a component according to a further embodiment of the application in cross section. The optical element 50 here takes the form of a reflector (52) and comprises a reflective filler. The reflective filler may make up 10% to 80% by weight, especially 20% to 60% by weight, of the optical element 50 and may be selected, for example, from $TiO_2$, $ZrO_2$, $Al_2O_3$ and combinations thereof. The optical element 50 may, as shown in FIG. 5, line at least part of the recess 25 and hence reflect the radiation produced, which increases the radiation yield.

Alternatively, the optical element 50 may also form part of the housing 20. The housing 20 may also be manufactured entirely from the polymer material of the optical element 50 and in that case includes a reflective filler at least in the region of the recess 25.

The semiconductor chip 10 in this example has been encapsulated with an encapsulation 51, and the encapsulation 51 may again be an optical element according to at least one embodiment of the application.

This patent application claims the priority of German patent application 10 2012 104 363.9, the disclosure content of which is hereby incorporated by reference.

The invention is not limited to the working examples by the description with reference thereto. Instead, the invention encompasses every novel feature and every combination of features, which especially includes every combination of features in the claims and every combination in the working examples, even if this feature or this combination itself is not specified explicitly in the claims or working examples.

The invention claimed is:

1. An optoelectronic component comprising:
   a housing;
   a radiation-emitting or radiation-receiving semiconductor chip disposed within the housing; and
   an optical element containing a polymer material comprising a silicone,
   wherein the silicone contains at least 40% by weight of cyclic siloxanes and at least 40% of the silicon atoms in the cyclic siloxanes are crosslinked via alkylene and/or alkylarylene groups to a further silicon atom in the silicone,
   wherein the optical element is obtainable by curing a composition comprising a first cyclic siloxane represented by the formula II and a second cyclic siloxane represented by the formula III

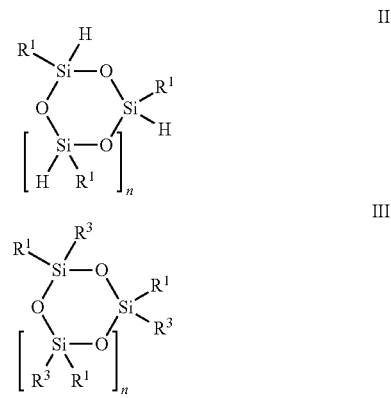

where, in formula II or in formula III,
n is in each case independently selected from 1, 2, 3, 4 and 5,
$R^1$ is in each case independently selected from a group comprising alkyl, cycloalkyl and aryl, and
$R^3$ is in each case independently a substituent which is represented by the formula

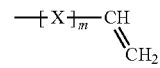

with m=0 or 1 and X=$C_1$-$C_4$-alkylene or phenylene, wherein the ratio of first cyclic siloxane to second cyclic siloxane in the composition is in the range from 2.5:1 to 4:1, wherein the optical element is arranged in the radiation path of the semiconductor chip and over the semiconductor chip, and wherein the optical element surrounds the semiconductor chip, wherein the optical element is transparent to the radiation used in the component with a relative transmission of at least 80%, and wherein the optical element comprises one or more converter materials for conversion of the radiation emitted by the semiconductor chip, which are embedded in the composition.

2. The component according to claim 1,
wherein at least 50% of the silicon atoms in the cyclic siloxanes are crosslinked via alkylene and/or alkylarylene groups to a further silicon atom in the silicone.

3. The component according to claim 1,
wherein the silicone contains at least 75% by weight of cyclic siloxanes.

4. The component according to claim 1,
wherein the cyclic siloxanes are represented by a structure of the formula I

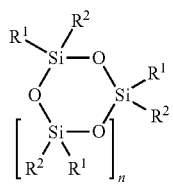

where
n is selected from 1, 2, 3, 4 and 5,
$R^1$ is in each case independently selected from a group comprising alkyl, cycloalkyl and aryl,
$R^2$ is in each case independently selected from a group comprising alkylene and/or alkylarylene group, hydrogen atom, a substituent of the formula

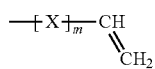

with m=0 or 1 and X=$C_1$-$C_4$-alkylene or phenylene, and an attached heteroatom, and where at least 40% of the $R^2$ substituents correspond to the alkylene and/or alkylarylene group, through which the $R^2$-substituted silicon atom in the cyclic siloxane of the formula I is crosslinked to a further silicon atom in the silicone, and the alkylene and/or alkylarylene group in each case independently has a structure of the following formula

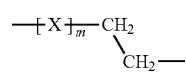

with m=0 or 1 and X=$C_1$-$C_4$-alkylene or phenylene.

5. The component according to claim 4,
wherein $R^1$ is each case independently selected from a group comprising $C_1$-$C_4$-alkyl, $C_5$-$C_6$-cycloalkyl and phenyl.

6. The component according to claim 4,
wherein at least 40% of the $R^1$ substituents are each independently selected from a group comprising $C_5$-$C_6$-cycloalkyl and phenyl.

7. The component according to claim 6,
wherein the refractive index n of the silicone is greater than or equal to 1.44.

8. The component according to claim 1,
wherein the optical element is an encapsulation which surrounds the semiconductor chip.

9. The component according to claim 1,
wherein the optical element comprises an inorganic filler embedded in the polymer material and selected from a group comprising thermally conductive particles, a diffuser, a converter material and a combination thereof.

10. The component according to claim 1,
wherein the optical element takes the form of a reflector and comprises a reflective filler.

11. The component according to claim 10,
wherein the housing has a recess in which the semiconductor chip is disposed, and the optical element lines at least part of the recess or forms at least part of the housing in the region of the recess.

12. A process for producing an optoelectronic component having an optical element, comprising the steps of:
A) providing a housing;
B) disposing a radiation-emitting or radiation-detecting semiconductor chip within the housing;
C) producing an optical element containing a polymer material comprising a silicone;
wherein the silicone contains at least 40% by weight of cyclic siloxanes and at least 40% of the silicon atoms in the cyclic siloxanes are crosslinked via alkylene and/or alkylarylene groups to a further silicon atom in the silicone,
wherein the optical element is produced in step C) by curing a composition comprising a first cyclic siloxane represented by the formula II and a second cyclic siloxane represented by the formula III

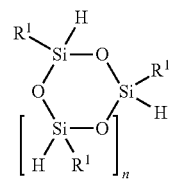

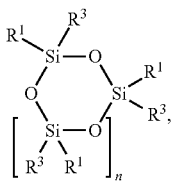

where, in formula II or in formula III,
n is in each case independently selected from 1, 2, 3, 4 and 5, R¹ is in each case independently selected from a group comprising alkyl, cycloalkyl and aryl, and R³ is in each case independently a substituent which is represented by the formula

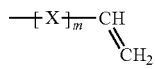

with m=0 or 1 and X=$C_1$-$C_4$-alkylene or phenylene, wherein the ratio of first cyclic siloxane to second cyclic siloxane in the composition is in the range from 2.5:1 to 4:1, wherein the optical element is arranged in the radiation path of the semiconductor chip and over the semiconductor chip, and wherein the optical element surrounds the semiconductor chip, wherein the optical element is transparent to the radiation used in the component with a relative transmission of at least 80%, and wherein the optical element comprises one or more converter materials for conversion of the radiation emitted by the semiconductor chip, which are embedded in the composition.

* * * * *